United States Patent [19]
Hutchins et al.

[11] Patent Number: 6,060,024
[45] Date of Patent: May 9, 2000

[54] AUTOMATIC DISSOLUTION TESTING SYSTEM

[75] Inventors: Burleigh M. Hutchins, Milford; Randall B. Rubinstein, Sharon; Barry T. Hixon, Franklin; William J. Buote, Natick, all of Mass.

[73] Assignee: Zymark Corporation, Hopkinton, Mass.

[21] Appl. No.: 08/204,119

[22] Filed: Mar. 1, 1994

Related U.S. Application Data

[62] Division of application No. 08/091,848, Jul. 14, 1993, abandoned.

[51] Int. Cl.[7] .......................... G01N 19/00; G01N 35/02
[52] U.S. Cl. .......................... 422/81; 422/100; 436/180; 436/508; 73/866
[58] Field of Search ............................... 422/81, 100, 102, 422/99; 436/180, 508; 73/866

[56] References Cited

U.S. PATENT DOCUMENTS

| | | | |
|---|---|---|---|
| 4,279,860 | 7/1981 | Smolen | 422/63 |
| 4,578,244 | 3/1986 | Cosgrove et al. | 422/65 |
| 4,754,657 | 7/1988 | Schneider | 73/866 |
| 4,924,716 | 5/1990 | Schneider | 73/866 |

*Primary Examiner*—Harold Pyon
*Attorney, Agent, or Firm*—John E. Toupal; Harold G. Jarcho

[57] ABSTRACT

A dissolution testing system including a base; a plurality of vessels mounted on the base; an agitation mechanism for agitating a liquid content of the vessels; and a head supported above each of the vessels and operable to automatically inject a liquid media into the vessel.

42 Claims, 6 Drawing Sheets

6,060,024

AUTOMATIC DISSOLUTION TESTING SYSTEM

This application is a divisional of U.S. Ser. No. 08/091,848, filed Jul. 14, 1993, now abandoned.

BACKGROUND OF THE INVENTION

In pharmaceutical laboratories, dissolution testing is playing an increasingly important role. Such testing determines the amount of active substance in a pharmaceutical formulation unit given off to a defined medium within a defined period of time. The active substance is generally contained in a pharmaceutical dosage form such as a capsule, tablet, coated tablet or the like, which is used as a therapeutic agent. Typically, a dissolution test is run in a vessel that contains a known volume of media which is usually DI water kept at a temperature of 37C. The active substance is dropped into the vessel of media and a paddle is spun to gently agitate the media. Samples are removed periodically and injected into analyzer equipment such as UV cells, fraction collectors or HPLC systems. After completion of a test cycle, the vessels are thoroughly washed before initiation of a subsequent cycle. Because most of the operational procedures are performed manually, current dissolution testing is highly labor intensive.

The object of this invention, therefore, is to provide an improved dissolution testing system that more efficiently performs desired test procedures.

SUMMARY OF THE INVENTION

The invention is a dissolution testing system including a base; a plurality of vessels mounted on the base; an agitation mechanist for agitating a liquid content of the vessels; and a head supported above each of the vessels and operable to automatically inject a liquid media into the vessel. The provision of heads that automatically inject liquid into each test vessel significantly reduces the labor requirements of a test cycle.

According to one feature of the invention, the head further includes a spray nozzle for introducing a cleaning liquid into the vessel. Automatic washing further reduces the labor intensiveness of the process.

According to other features of the invention, each head includes a fill nozzle disposed to direct the liquid media into the vessel, fill tubing providing communication between the fill nozzle and a source of liquid media, and wash tubing providing communication between the spray nozzle and a source of cleaning liquid. The wash and fill tubings facilitate the introduction of liquid media and cleaning liquid into the vessel.

According to yet another feature of the invention, each head further includes an adjustment nozzle for injecting a pH adjustment solution into the vessel. Additional labor savings are provided by the adjustment mechanism.

According to further features of the invention, the fill and adjustment nozzles are disposed, respectively, to direct the source of liquid media and the adjustment solution against a sidewall portion of the vessel. Undesirable splashing of liquid is reduced by the transversely oriented nozzles.

According to yet additional features of the invention, each head further includes a sampling mechanism for withdrawing a liquid sample from the vessel, and an aspiration mechanism for removing the liquid content of the vessel. Additional labor savings are promoted by the sampling and aspiration mechanisms.

According to still other features of the invention, the sampling mechanism includes a sampling probe for withdrawing the liquid sample and a sampling drive for moving the sampling probe into and out of the vessel; and the aspiration mechanism includes an aspiration probe for removing the liquid content and an aspiration drive for moving the aspiration probe into and out of the vessel. These features facilitate desired sample removal and aspiration of the vessels.

According to yet another feature of the invention, each head further includes a detector for detecting the temperature of a liquid content of the vessel. Controlled dissolution testing is enhanced by the temperature detector.

According to a further feature of the invention, each head includes a dispenser for automatically dispensing a solid sample into the vessel. Automatic dispensing of solid samples further reduces the manual labor requirements of the system.

DESCRIPTION OF THE DRAWINGS

These and other objects and features of the invention will become more apparent upon a perusal of the following description taken in conjunction with the accompanying drawings wherein.

DESCRIPTION OF THE INVENTION

Figure 6:
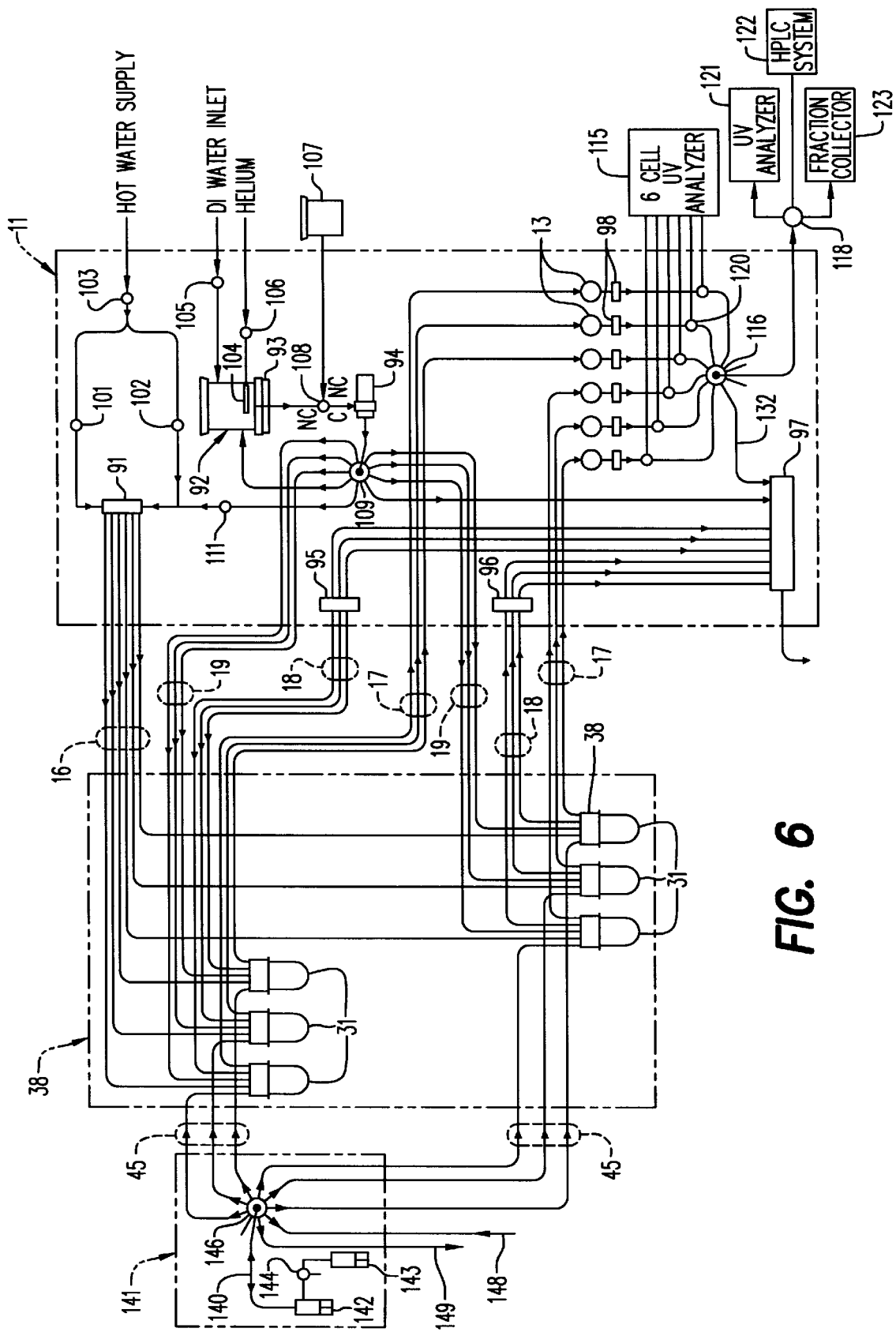
FIG. 6 is a schematic diagram of a dissolution testing system according to the invention.

A control unit 11 (FIG. 1) includes a cabinet 12 retaining a plurality of fluid pumps 13, a liquid filter holding mechanism 14 and a dispenser mechanism 15 for dispensing filters into the filter holding mechanism 14. Extending out of the cabinet 12 are a plurality of sets 20 of lines, only one set being shown. Each set 20 includes a spray wash line 16, a sampling line 17, a waste aspirate line 18, a media fill line 19 and electrical cable 21. An output coupling 22 is provided for transmitting test samples to analyzer equipment. Other components retained within the cabinet 12 are illustrated in FIG. 6.

Figure 2:
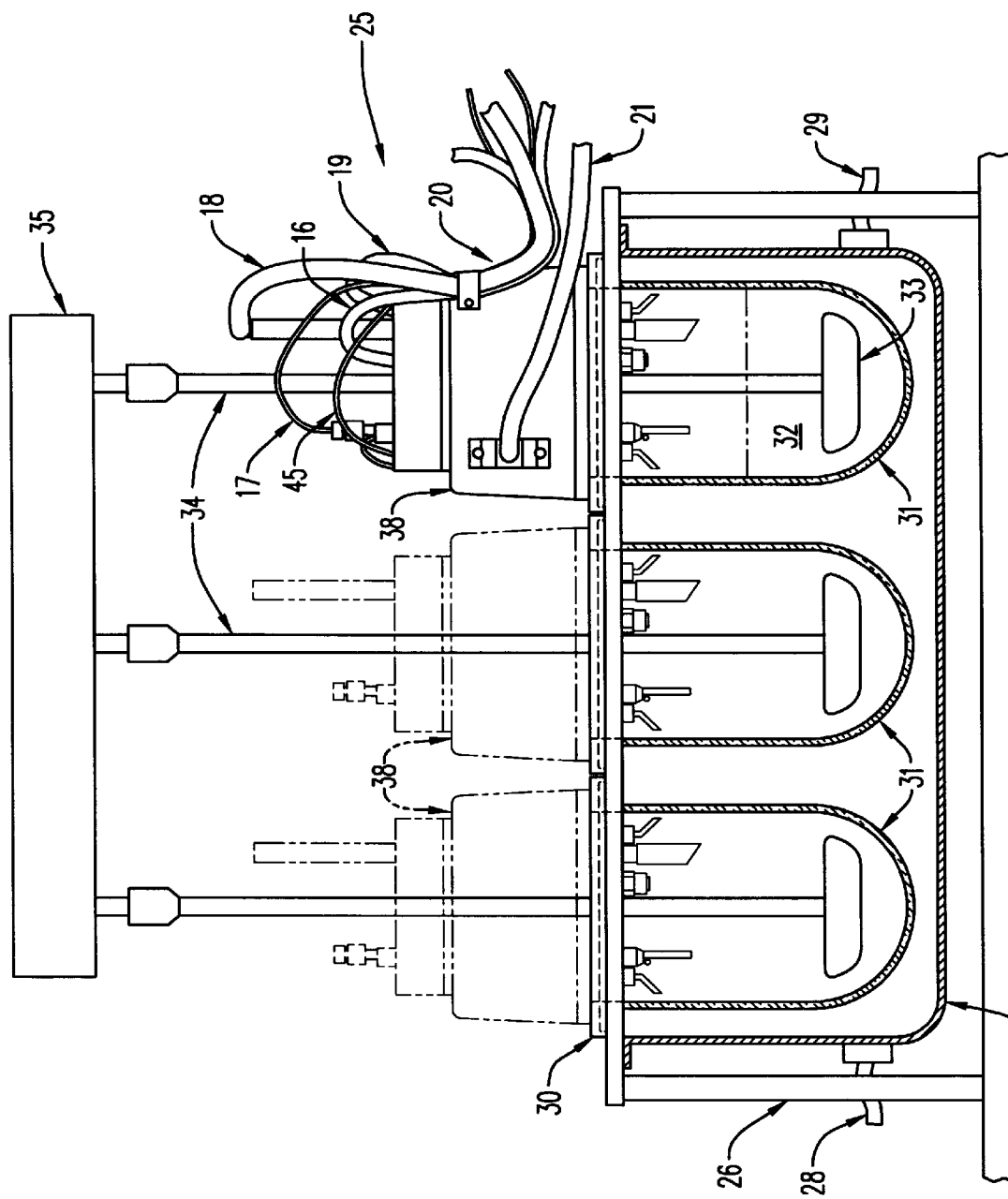
FIG. 2 is a front view, partially in cross section, of a test assembly for the system.

A test assembly 25 (FIG. 2) includes a rack base 26 that supports a liquid reservoir 27 having an inlet 28 and an outlet 29 for circulating heating water. Also mounted on the rack base 26 and extending into the liquid reservoir 27 so as to be heated thereby are six two dimensionally aligned open upper ended vessels 31, only three of which are shown. Each of the vessels 31 receives a quantity of liquid media 32 that is heated by water in the reservoir 27. The liquid media 32 in each vessel 31 is agitated by a paddle 33 rotated by a shaft 34 driven by a paddle drive assembly 35. Mounted over each of the vessels 31 on a base plate 30 is a control head 38, only one of which is shown in detail. Liquid communication between the control unit 11 and each of the control heads 38 is provided by one of the line sets 20 including a wash line 16, a sampling line 17, a waste aspirate line 18 and a media fill line 19. Also extending between the control unit 11 and each control head 38 and providing electrical communication therebetween is an electrical cable 21.

Figure 3:
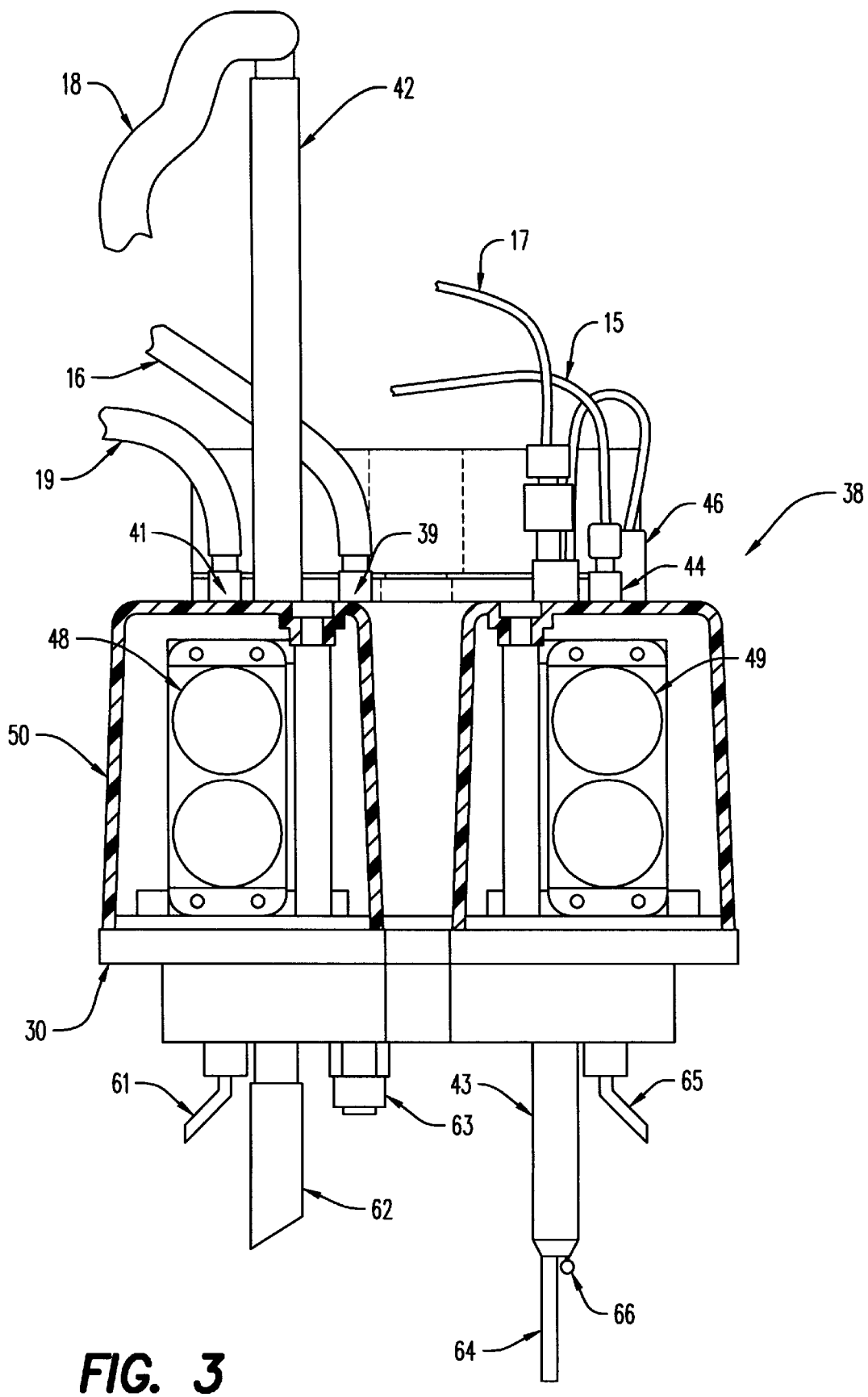
FIG. 3 is a rear view, partially in cross section, of a control head shown in FIG. 2.
Figure 4:
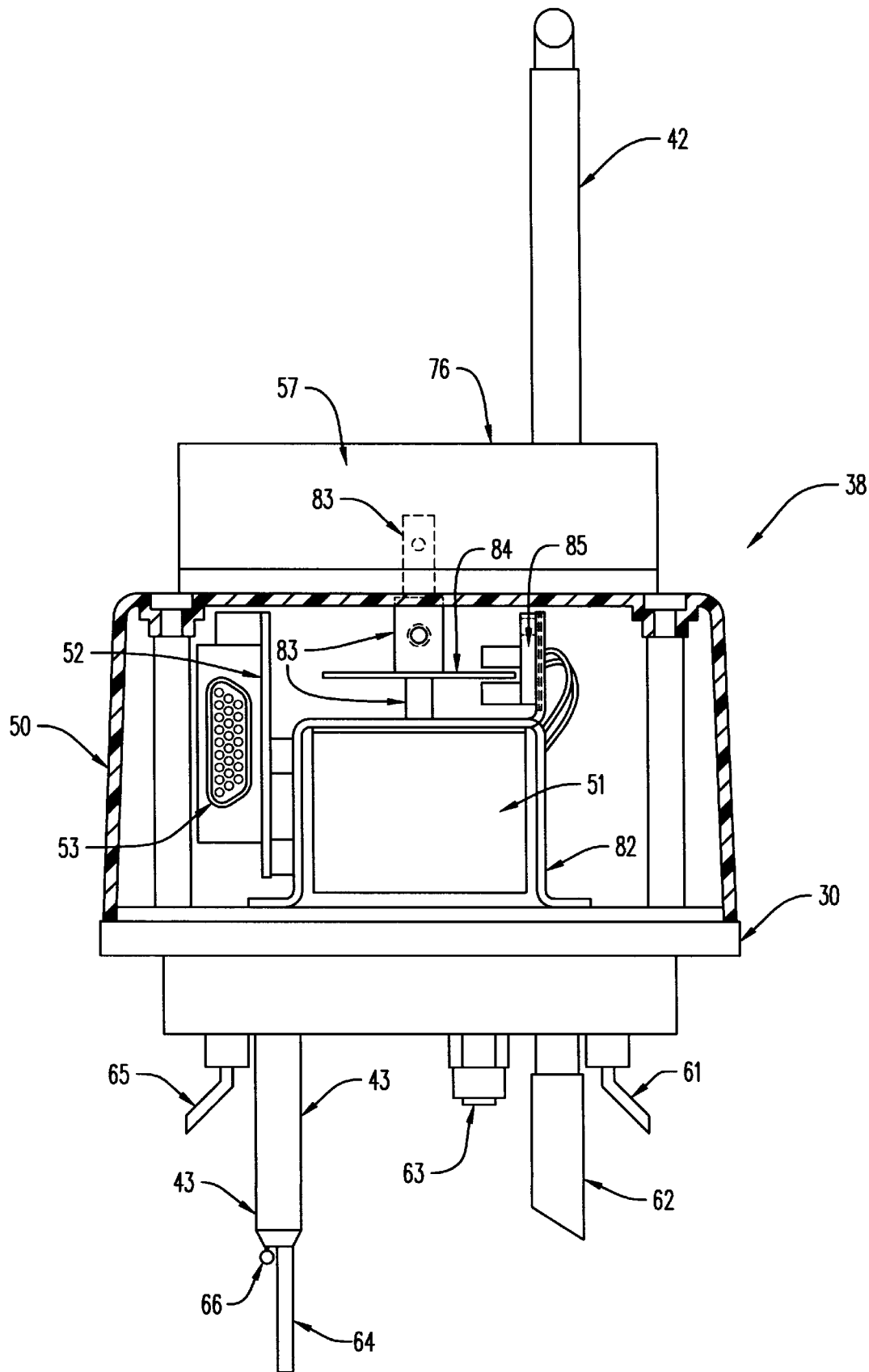
FIG. 4 is a front view, partially in cross section of the control head shown in FIG. 3.
Figure 5:
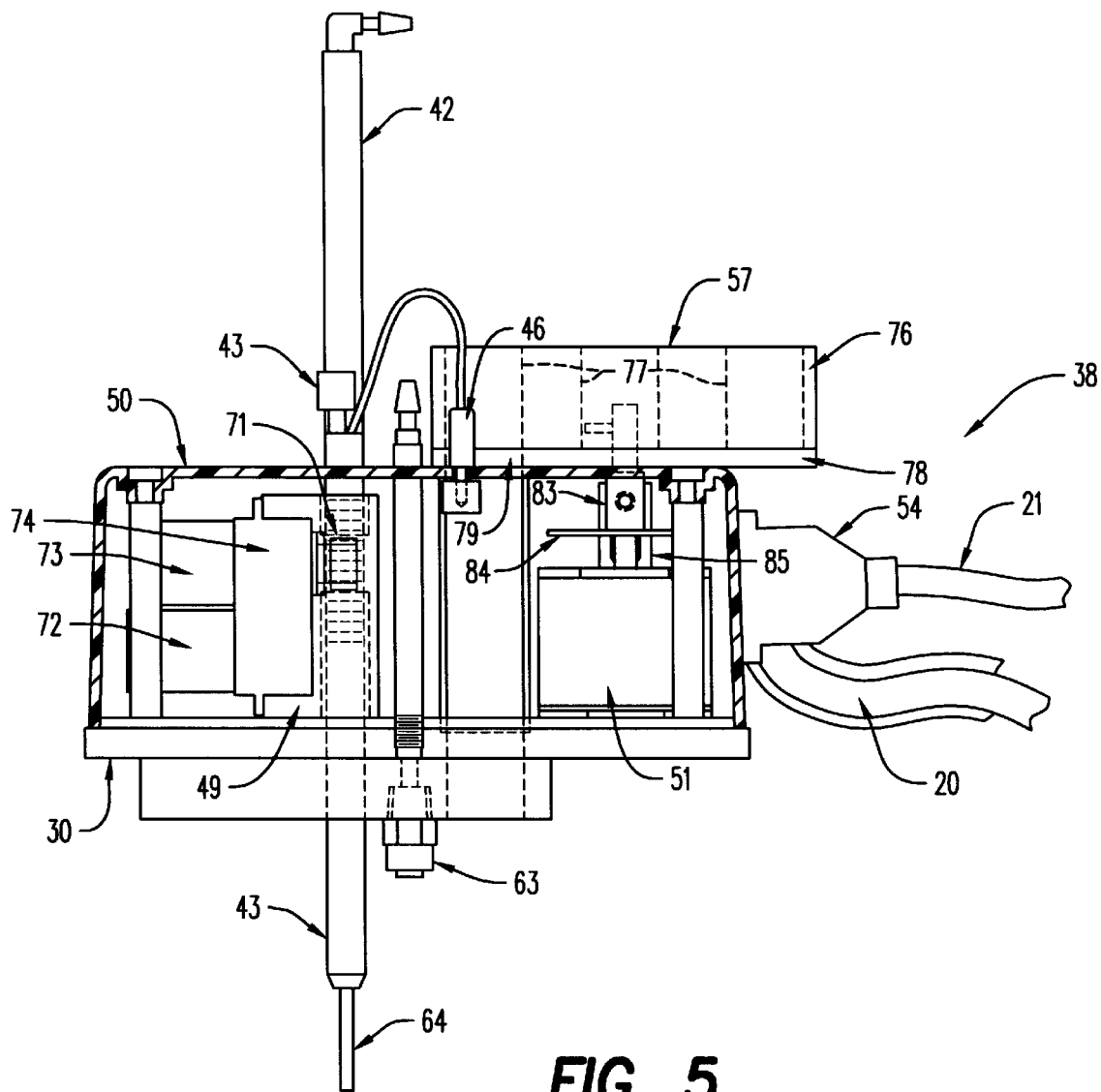
FIG. 5 is a left side view, partially in cross section of the control head shown in FIGS. 3 and 4.

The control head 38 is shown in greater detail in FIGS. 3–5. Retained by the control head 38 is a spray wash tube 39 connected to the spray wash line 16, a media fill tube 41 connected to the fill line 19, an aspiration probe 42 connected to the aspirate line 18, a sampling probe 43 connected to the sampling line 17, a pH adjustment and media replacement tube 44 connected to a pH adjustment and media replacement line 45 and a temperature detector 46. Also retained by the control head 38 is an aspiration probe drive mechanism 48, a sample probe drive mechanism 49 (FIG. 3), a stepping motor 51 (FIG. 4) and an interconnect board 52. Connected to the interconnect board 52 is a cable connector 53 that receives a plug 54 (FIG. 5) on the electrical cable 21. The head is covered by a cover 50.

A sample tablet dispenser 57 is mounted on the control head 38 and is coupled to the stepping motor 51. Attached to lower ends of the wash tube 39, the fill tube 41, the aspiration probe 42, the sampling probe 43 and the adjustment and replacement tubing 44, respectively, are a spray wash nozzle 63, an outwardly directed fill nozzle 61, an aspiration tip 62, a sampling tip 64 and an outwardly directed adjustment and replacement nozzle 65. A temperature sensing thermistor 66 of the temperature detector 46 is supported at a lower end of the sampling probe 43.

As shown in FIG. 5, the sampling probe drive mechanism 49 which is identical to the aspiration probe drive mechanism 48 includes a rack and gear drive 71 operatively coupled to the sampling probe 43, a servo motor 72, a position controlling potentiometer 73 and a gear box 74 coupling the servo motor 72 to the rack and gear drive 71. In response to appropriate energization of the servo motors 72, the rack and gear drives 71 produce reciprocating movement of the aspiration probe 42 and the sampling probe 43 into and out of the vessels 31.

The tablet dispenser 57 includes a receptacle 76 defining a plurality of circumferentially distributed stations 77, each for receiving a sample tablet to be dissolved in the liquid media 32 in the vessel 31. Rotatably supporting the receptacle 76 is a fixed plate 78 having an opening 79 aligned with a vertical passage 81 in the control head 38. The stepping motor 51 (FIG. 4) is mounted on a motor bracket 82 and is rotatably coupled to the receptacle 76 by a shaft 83 that also rotates a sensor disk 84. Also mounted on the motor bracket 82 is a photo detector 85 that senses the position of the sensor disk 84 and thereby the rotational position of the receptacle 76. In response to appropriate energization of the stepping motor 51, the receptacle 76 is sequentially rotated into positions that produce sequential registration between each of the stations 77 and the opening 79. As each station 77 registers with the opening 79, a sample tablet is discharged through the passage 81 into the vessel 31. The photo detector 85 detects when an initially empty home station returns into registration with the opening 79 thereby indicating a need to reload the receptacle 76.

Figure 1:
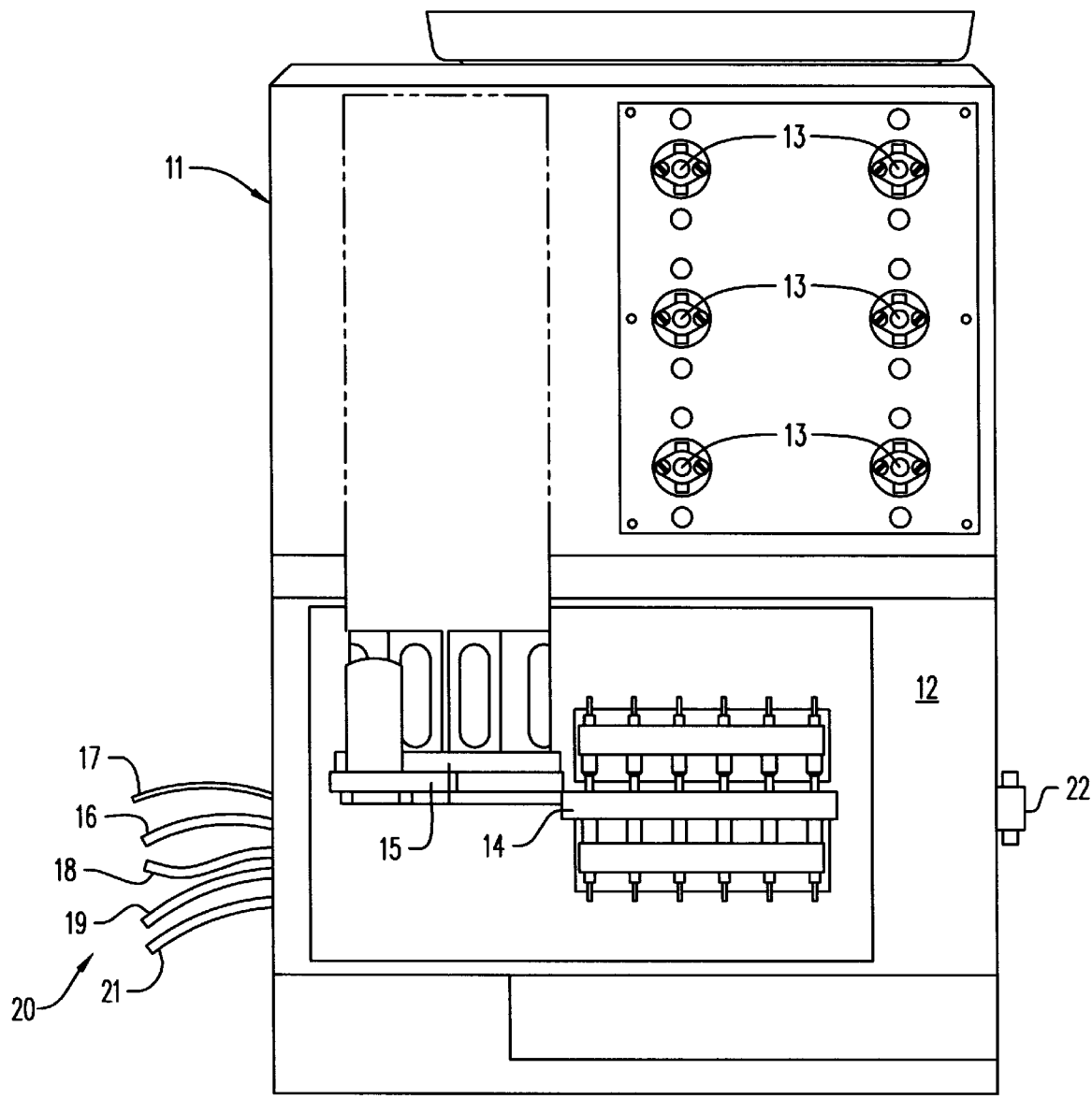
FIG. 1 is a front view of a control unit for the dissolution testing system of the invention.

As shown in FIG. 6, the control unit 11 (FIG. 1) retains a wash manifold 91, a media tank 92 supported on a balance 93, a media pump 94, a pair of waste pumps 95, 96, a waste manifold 97 and a plurality of sampling filters 98 retained by the filter holding mechanism 14 (FIG. 1). The wash manifold 91 has inlets connected to an external hot water supply by a pair of parallel valves 101, 102 and a regulator 103; and a plurality of outlets each connected to a different one of the wash lines 16. Communicating with the media tank 92 and a helium sparge unit 104 therein through, respectively, valves 105, 106 are an external water source and a helium source. Dissolved gases in the liquid media within the tank 92 are eliminated by the sparge unit 104.

The media pump 94 has an inlet connected to the media tank 92 by a three-way valve 108 which also connects an external media tank 107 to the tank 92. An outlet of the media pump 94 is connected to a multiple port dispensing valve 109, outlets of which are connected to the media fill lines 19, the wash manifold 91 by a valve 111 and the waste manifold 97. Receiving the waste lines 18 are inlets of the waste pumps 95, 96, the outlets of which are connected to the waste manifold 97. The sampling lines 17 are connected to the inlets of the sampling pumps 13, the outlets of which communicate through the filters 98 with either an external six cell UV analyzer 115 or the inlets of a multiple port valve 116. Outlets of the valve 116 communicate either with the waste manifold 97 or an external valve 118 alternatively feeding either a UV analyzer 121, an HPLC system 122 or a fraction collector 123.

OPERATION

To initiate a test sequence, the media pump 94 is energized producing a flow of liquid media from the tank 92 through the valves 108 and 109, the fill lines 19, and the fill tubings 41 for discharge out of the nozzles 61 into the vessels 31. The amount of media flow is controlled by the balance 93 and the outward orientation of the nozzles 61 reduces splashing and air entrainment within the media samples collected in the vessels 31. Next, the sampling probes 43 are moved downwardly into each of the vessels 31 allowing the thermistor sensors 66 to monitor the temperature of the liquid media 32 in each vessel. Once a desired temperature is obtained, the stepping motors 51 (FIG. 5) are either serially or simultaneously energized to produce registration of a filled station 77 of the receptacles 76 with the openings 79 in the plates 78 resulting in a release of a solid sample tablet into each of the vessels 31. During a dissolution period, the paddles 33 are activated to produce agitation of the liquid media 32 in each of the vessels 31.

To effect sampling during a given dissolution cycle, the sample probes 43 are lowered and the sampling pumps 13 are energized to withdraw a predetermined liquid sample from each of the vessels 31 through the sampling tips 64, the sampling tubes 42, the sampling lines 17 and the sampling filters 98 either individually into the six cell UV analyzer 115 or collectively into the valve 116 for discharge into one of the analyzer systems 121–123. Any excess media sample is discharged through a line 132 into the waste manifold 97. Once all desired sampling tests have been completed, the aspiration probe drive mechanisms 48 are activated to lower the aspiration probes 42 into the vessels 31. Energization of the waste pumps 95, 96 institutes aspiration of the vessels 31 through the aspiration tips 62 and the aspiration lines 18 into the waste manifold 97.

After all the vessels 31 have been emptied, the valves 101, 102 are opened to produce the flow of hot water through the wash manifold 91 and the wash lines 16 for discharge through the spray nozzles 63 to thoroughly clean the vessels 31. The expended cleaning liquid is discharged into the waste manifold 97 via the aspiration probes 42 and the aspiration lines 18 by the still energized waste pumps 95, 96. To prevent dilution of liquid media subsequently dispensed into the vessels 31 by any wash water remnant therein, the media pump 94 then is energized to produce media flow through an outlet of the valve 109 and the valve 111, the wash manifold 91 and the wash lines 16 and resulting in discharge of media through the spray nozzle 63. The sprayed media collects any water remnant therein and the combined liquid then is removed by the energized waste pumps 95, 96.

Also provided in the dissolution system is a pH adjustment and media replacement unit 141 shown in FIG. 6. Included in the unit 141 is a liquid handling syringe 142 and an air push syringe 143 connected by a 3-way valve 144. The output of the liquid syringe 142 is connected to a port of a multiple port valve 146 having outlet ports connected by the adjustment lines 45 to the media adjustment tubes 44 in the control heads 38. Facilitated by the unit 141 is either selective adjustment of the media pH in the vessels 31 or replacement of media that has been removed for sample testing so as to maintain a constant media volume within the vessels 31.

To initiate a media replacement operation, the valve 146 is moved into a position that provides communication between a fill line 148 and the liquid syringe 142. Next, the liquid syringe 142 is activated to accumulate a media charge of predetermined volume, and the air push syringe 143 is activated to accumulate a charge of air. After positioning of the valve 146 to connect the line 140 with an adjustment line 45 associated with a particular vessel 31, the liquid syringe 142 is activated to induce an appropriate flow of replacement media into the selected vessel 31 through the lines 140 and 45. Full delivery of the media replacement charge is provided by activation of the air syringe 143 to cause air flow through the valve 144, the liquid syringe 142 and the lines 140 and 45. Any excess material can be removed through a waste line 49 connected to the valve 146. The unit 141 can be waste in the same manner to adjust the pH of the media content of the vessels 31. For pH adjustment, a suitable buffered solution is drawn into the liquid syringe 142 through the fill line 148 for ultimate discharge into the vessels 31.

Obviously, many modifications and variations of the present invention are possible in light of the above teachings. It is to be understood, therefore, that the invention can be practiced otherwise than as specifically described.

What is claimed is:

1. A dissolution testing system comprising:
   base means;
   a plurality of vessels mounted in situ on said base means;
   agitation means for agitating a liquid content of said vessels; said agitation means comprising a paddle disposed in each vessel, a drive shaft coupled to each paddle, and drive means for rotating said drive shafts; and
   head means supported above each of said plurality of vessels and comprising fill means operable to automatically inject a liquid media into said vessel; said head means further comprising liquid media handling means mounted for movement relative to said vessel and said shaft therein, said movement having a component parallel thereto.

2. A system according to claim 1 wherein each said head means is disposed between said vessel and said drive means.

3. A system according to claim 2 wherein said head means further comprises an adjustment means for automatically injecting pH adjustment solution into said vessel in situ.

4. A system according to claim 3 wherein said head means further comprises wash means for introducing a cleaning liquid into said vessel in situ.

5. A system according to claim 2 wherein said media handling means comprises sampling means for automatically withdrawing a liquid sample from said vessel in situ.

6. A system according to claim 5 wherein said sampling means comprises a sampling probe for withdrawing the liquid sample and sampling drive means for moving said sampling probe into and out of said vessel independently of said paddle therein.

7. A system according to claim 2 wherein said media handling means comprises aspiration means for automatically removing the liquid content of said vessel in situ.

8. A system according to claim 7 wherein said aspiration means comprises an aspiration probe for removing the liquid content and aspiration drive means for moving said aspiration probe into and out of said vessel independently of said paddle therein.

9. A system according to claim 2 wherein said head means further comprises detector means for detecting the temperature of a liquid content of said vessel.

10. A system according to claim 9 wherein said detector means comprises a temperature sensor adapted for movement into and out of said vessel.

11. A system according to claim 2 wherein each said drive shaft extends through said head means disposed between said vessel and said drive means.

12. A system according to claim 11 wherein said head means comprises a housing means retaining at least a portion of said handling means and defining a passage receiving said drive shaft.

13. A system according to claim 12 wherein each said paddle is fixed in a given position within said vessel.

14. A system according to claim 2 wherein said fill means comprises a fill nozzle disposed to inject the liquid media into said vessel and fill tubing providing communication between said fill nozzle and a source of liquid media.

15. A system according to claim 14 wherein said fill nozzle is disposed to direct the liquid media against a sidewall portion of said vessel.

16. A system according to claim 14 wherein said head means further comprises wash means for automatically introducing a cleaning liquid into said vessel in situ.

17. A system according to claim 16 wherein said wash means comprises a spray nozzle disposed to spray the cleaning liquid into said vessel and wash tubing providing communication between said spray nozzle and a source of cleaning liquid.

18. A system according to claim 17 wherein said head means further comprises an adjustment means for automatically injecting a pH adjustment solution into said vessel in situ.

19. A system according to claim 18 wherein said adjustment means comprises an adjustment nozzle disposed to inject the adjustment solution into said vessel.

20. A system according to claim 19 wherein said adjustment nozzle is disposed to direct the adjustment solution against a sidewall portion of said vessel.

21. A system according to claim 2 wherein said head means further comprises dispenser means for automatically dispensing a solid sample into said vessel.

22. A system according to claim 21 wherein said media handling means comprises sampling means for withdrawing a liquid sample from said vessel in situ.

23. A system according to claim 22 wherein said media handling means further comprises detector means for detecting the temperature of a liquid content of said vessel.

24. A system according to claim 23 wherein said sampling means comprises a sampling probe for withdrawing the liquid sample and sampling drive means for moving said sampling probe into and out of said vessel.

25. A system according to claim 24 wherein said detector means comprises a temperature sensor mounted on said sampling probe.

26. A system according to claim 25 wherein said media handling means further comprises aspiration means for automatically removing the liquid content of said vessel in situ.

27. A system according to claim 26 wherein said head means further comprises wash means for automatically introducing a cleaning liquid into said vessel in situ.

28. A system according to claim 25 wherein said head means further comprises an adjustment means for automatically injecting a Ph adjustment solution into said vessel in situ.

29. A system according to claim 28 including a media source, and multiple port fill valve means connecting said media source to said fill means in each said head means.

30. A system according to claim 29 including analyzer means, and multiple port sample valve means connecting said analyzer means to said sampling means in each of said head means.

31. A system according to claim 30 including a cleaning liquid source connected to said spray nozzle in each of said head means.

32. A system according to claim 31 including a pH adjustment solution source and multiple port adjustment valve means connecting said solution source to said adjustment means in each of said head means.

33. A dissolution testing system comprising:

base means;

a plurality of vessels mounted on said base means;

agitation means for agitating a liquid content of said vessels; said agitation means comprising a paddle disposed in each vessel, a drive shaft coupled to each paddle, and drive means for rotating said drive shafts; and head means supported above each of said plurality of vessels and comprising a temperature sensor for detecting the temperature of a liquid content of said vessel, said sensor being mounted for movement relative to said vessel and said paddle therein, said movement having a component parallel thereto.

34. A system according to claim 33 wherein said head means further comprises sampling means for automatically withdrawing a liquid sample from said vessel.

35. A system according to claim 34 wherein said sampling means comprises a sampling probe for withdrawing the liquid sample and sampling drive means for moving said sampling probe into and out of said vessel independently of said paddle therein.

36. A system according to claim 35 wherein said temperature sensor is mounted on said sampling probe.

37. A dissolution testing system comprising:

base means;

a plurality of vessels mounted on said base means;

agitation means for agitating a liquid content of said vessels; said agitation means comprising a paddle disposed in each vessel, a drive shaft coupled to each paddle, and drive means for rotating said drive shafts; and head means supported above each of said plurality of vessels and comprising sampling means for automatically withdrawing a liquid sample from said vessel, said sampling means being mounted for movement relative to said vessel and said paddle therein, said movement having a component parallel thereto.

38. A system according to claim 37 wherein said sampling means comprises a sampling probe for withdrawing the liquid sample and sampling drive means for moving said sampling probe into and out of said vessel independently of said paddle therein.

39. A dissolution testing system comprising:

base means;

a plurality of vessels mounted on said base means;

agitation means for agitating a liquid content of said vessels; said agitation means comprising a paddle disposed in each vessel, a drive shaft coupled to each paddle, and drive means for rotating said drive shafts; and head means supported above each of said plurality of vessels and aspiration means for automatically removing the liquid content of said vessel, said aspiration means being mounted for movement relative to said vessel and said paddle therein, said movement having a component parallel thereto.

40. A system according to claim 39 wherein said aspiration means comprises an aspiration probe for removing the liquid content and aspiration drive means for moving said aspiration probe into and out of said vessel independently of said paddle therein.

41. A dissolution testing system comprising:

base means;

a plurality of vessels mounted in situ in said base means;

agitation means for agitating a liquid content of said vessels;

head means supported above each of said plurality of vessels and comprising fill means operable to automatically inject a liquid media into said vessel, and sampling means for automatically withdrawing a liquid sample from said vessel in situ; and wash means for automatically introducing a cleaning liquid into each said vessel in situ.

42. A system according to claim 41 wherein said wash means comprises a spray nozzle disposed to spray the cleaning liquid into said vessel and wash tubing providing communication between said spray nozzle and a source of cleaning liquid.

* * * * *

UNITED STATES PATENT AND TRADEMARK OFFICE
CERTIFICATE OF CORRECTION

PATENT NO : 6,060,024
DATED : May 9, 2000
INVENTOR(S): Hutchins et al

It is certified that error appears in the above-identified patent and that said Letters Patent are hereby corrected as shown below:

Column 1, line 34, "mechanist" should read --mechanism--.

Signed and Sealed this

Fifteenth Day of May, 2001

Attest:

NICHOLAS P. GODICI

Attesting Officer     Acting Director of the United States Patent and Trademark Office